(12) United States Patent
Kottenstette et al.

(10) Patent No.: US 12,070,283 B2
(45) Date of Patent: Aug. 27, 2024

(54) INTERLOCKING SYSTEM AND METHOD FOR JOYSTICKS IN A CATHETER PROCEDURE SYSTEM

(71) Applicant: Corindus, Inc., Waltham, MA (US)

(72) Inventors: Nicholas Kottenstette, Worcester, MA (US); Per Bergman, West Roxbury, MA (US); Yao Li, Belmont, MA (US); Seth Hunter, Waltham, MA (US); Adam Young, Dedham, MA (US)

(73) Assignee: Corindus, Inc., Newton, MA (US)

( * ) Notice: Subject to any disclaimer, the term of this patent is extended or adjusted under 35 U.S.C. 154(b) by 514 days.

(21) Appl. No.: 17/443,565

(22) Filed: Jul. 27, 2021

(65) Prior Publication Data
US 2021/0353376 A1 Nov. 18, 2021

Related U.S. Application Data

(63) Continuation of application No. 16/290,309, filed on Mar. 1, 2019, now Pat. No. 11,109,921, which is a
(Continued)

(51) Int. Cl.
*A61B 34/30* (2016.01)
*A61B 5/055* (2006.01)
(Continued)

(52) U.S. Cl.
CPC .............. *A61B 34/30* (2016.02); *A61B 5/055* (2013.01); *A61B 6/032* (2013.01); *A61B 6/503* (2013.01);
(Continued)

(58) Field of Classification Search
CPC ........ A61B 2034/301; A61B 2034/742; A61B 34/74; A61B 34/30; A61B 34/25; A61B 34/37; A61B 34/00
See application file for complete search history.

(56) References Cited

U.S. PATENT DOCUMENTS

| 3,922,996 A | 12/1975 | Meyer |
| 4,706,671 A | 11/1987 | Weinrib |

(Continued)

FOREIGN PATENT DOCUMENTS

| CN | 101427205 | 5/2009 |
| CN | 102124425 | 7/2011 |

(Continued)

OTHER PUBLICATIONS

PCT International Search Report and Written Opinion for PCT/US2017/031921; mail date Jul. 19, 2017; 9 pages.
(Continued)

*Primary Examiner* — Quynh-Nhu H. Vu

(57) ABSTRACT

An interlocking system for a joystick in a catheter procedure system includes a joystick configured to generate a first voltage output signal based on a linear activation of the joystick and a second voltage output signal based on a rotational activation of the joystick. A joystick cover is disposed over the joystick and includes an upper portion having an electrode plating on an inner surface of the upper portion and a lower portion having an inner surface. A capacitive touch detection circuit is coupled to the electrode plating of the upper portion of the joystick cover and is mounted on the inner surface of the lower portion of the joystick cover. The capacitive touch detection circuit is configured to detect a proximal change in capacitance in the electrode plating of the upper portion of the joystick cover and to generate a touch output signal to indicate whether a change in capacitance has been detected. A signal enable circuit is coupled to the joystick and the capacitive touch detection circuit and is configured to generate a linear enable voltage output signal and a rotational enable voltage output signal based on whether a change in capacitance has been detected.

18 Claims, 7 Drawing Sheets

Related U.S. Application Data continuation of application No. 15/193,370, filed on Jun. 27, 2016, now Pat. No. 10,245,112.

(51) Int. Cl.

| | |
|---|---|
| *A61B 6/00* | (2024.01) |
| *A61B 6/03* | (2006.01) |
| *A61B 6/50* | (2024.01) |
| *A61B 8/08* | (2006.01) |
| *A61B 17/00* | (2006.01) |
| *A61B 34/00* | (2016.01) |
| *A61B 34/37* | (2016.01) |
| *A61B 90/00* | (2016.01) |
| *A61M 25/01* | (2006.01) |
| *A61B 5/00* | (2006.01) |
| *A61B 6/12* | (2006.01) |

(52) U.S. Cl.
CPC ...... *A61B 8/0841* (2013.01); *A61B 17/00234* (2013.01); *A61B 34/37* (2016.02); *A61B 34/74* (2016.02); *A61B 90/37* (2016.02); *A61M 25/0105* (2013.01); A61B 5/0046 (2013.01); A61B 5/7475 (2013.01); A61B 6/12 (2013.01); A61B 8/0883 (2013.01); A61B 2017/00022 (2013.01); A61B 2017/00044 (2013.01); A61B 2034/301 (2016.02); A61B 2034/742 (2016.02); A61B 2090/374 (2016.02); A61B 2090/376 (2016.02); A61B 2090/3762 (2016.02); A61B 2090/378 (2016.02); A61B 2505/05 (2013.01)

(56) References Cited

U.S. PATENT DOCUMENTS

| | | | |
|---|---|---|---|
| 4,926,858 A | 5/1990 | Gifford et al. | |
| 5,217,474 A | 6/1993 | Zacca et al. | |
| 5,527,279 A | 6/1996 | Imran | |
| 5,854,622 A | 12/1998 | Brannon | |
| 5,880,718 A * | 3/1999 | Frindle | H03K 17/9622 |
| | | | 345/174 |
| 5,907,487 A | 5/1999 | Rosenberg et al. | |
| 6,490,490 B1 * | 12/2002 | Uchikubo | A61B 1/04 |
| | | | 700/246 |
| 6,569,086 B2 * | 5/2003 | Motoki | A61B 1/0016 |
| | | | 600/151 |
| 6,590,171 B1 | 7/2003 | Wolf et al. | |
| 6,726,675 B1 * | 4/2004 | Beyar | A61M 25/0105 |
| | | | 600/137 |
| 8,390,438 B2 | 3/2013 | Olson et al. | |
| 9,320,479 B2 | 4/2016 | Wenderow et al. | |
| 10,499,795 B2 * | 12/2019 | Ogawa | A61B 1/00133 |
| 2004/0011154 A1 | 1/2004 | Dybro | |
| 2004/0054254 A1 * | 3/2004 | Miyake | A61B 1/0051 |
| | | | 600/104 |
| 2004/0147934 A1 | 7/2004 | Kiester | |
| 2005/0119615 A1 | 6/2005 | Noriega et al. | |
| 2006/0074442 A1 | 4/2006 | Noriega et al. | |
| 2006/0243080 A1 | 11/2006 | Takamoto et al. | |
| 2008/0161801 A1 | 7/2008 | Steinke et al. | |
| 2009/0213073 A1 | 8/2009 | Obermeyer et al. | |
| 2009/0248042 A1 | 10/2009 | Kirschenman | |
| 2010/0010505 A1 | 1/2010 | Herlihy et al. | |
| 2010/0175701 A1 | 7/2010 | Reis et al. | |
| 2010/0274087 A1 | 10/2010 | Diolaiti et al. | |
| 2011/0237880 A1 | 9/2011 | Hamel et al. | |
| 2012/0001860 A1 | 6/2012 | Le | |
| 2013/0172906 A1 | 7/2013 | Olson et al. | |
| 2014/0194897 A1 | 7/2014 | Kirschenman et al. | |
| 2014/0277002 A1 | 9/2014 | Grace | |
| 2014/0277747 A1 | 9/2014 | Walker et al. | |
| 2015/0157497 A1 | 6/2015 | Hufford et al. | |
| 2016/0270780 A1 | 9/2016 | Hall et al. | |

FOREIGN PATENT DOCUMENTS

| | | |
|---|---|---|
| CN | 102292692 | 12/2011 |
| EP | 0974889 A1 | 1/2000 |
| EP | 2923669 B1 | 6/2017 |
| JP | 2006253000 | 9/2006 |
| JP | 2008515135 A | 5/2008 |
| JP | 2015037572 | 2/2015 |
| WO | 0161431 | 8/2001 |
| WO | 2003015428 A9 | 12/2003 |
| WO | 2007005976 A1 | 1/2007 |
| WO | 2010025338 A1 | 3/2010 |
| WO | 2011094877 | 8/2011 |

OTHER PUBLICATIONS

Sato et al., Touche': Enhancing Tough Interaction on Humans, Screens, Liquids, and Everyday Objects, CHI' 12, May 5-10, 2012, Austin, Texas, USA, Copyright 2012 ACM 978-1-4503-1015-Apr. 12, 2005, 10 pages.

European extended search report for EP 17820733.8; mail date Jan. 3, 2020; 9 pages.

EESR for EP Application 11833036.4; mail date Jun. 30, 2017; 12 pages.

International Preliminary Report on Patentability for PCT/US2011/053642; mail date Apr. 25, 2013; 12 pages.

International Search Report and Written Opinion for PCT/US2011/053642; mail date Jan. 17, 2012; 14 pages.

* cited by examiner

INTERLOCKING SYSTEM AND METHOD FOR JOYSTICKS IN A CATHETER PROCEDURE SYSTEM

CROSS-REFERENCE TO RELATED PATENT APPLICATIONS

This application is a continuation of U.S. patent application Ser. No. 16/290,309, filed Mar. 1, 2019, entitled "INTERLOCKING SYSTEM AND METHOD FOR JOYSTICKS IN A CATHETER PROCEDURE SYSTEM", which is a continuation of U.S. patent application Ser. No. 15/193,370, filed Jun. 27, 2016, now U.S. Pat. No. 10,245,112, entitled "INTERLOCKING SYSTEM AND METHOD FOR JOYSTICKS IN A CATHETER PROCEDURE SYSTEM", each of which is incorporated in its entirety for all purposes.

FIELD OF THE INVENTION

The present invention relates generally to the field of catheter systems for performing therapeutic procedures and in particular, to an interlocking system and method for joysticks in a catheter procedure system.

BACKGROUND OF THE INVENTION

Catheters may be used for many medical procedures, including inserting a guide wire, delivering a stent and delivering and inflating a balloon. Catheterization procedures are commonly performed for diagnosis and treatment of diseases of the heart and vascular systems. The catheterization procedure is generally initiated by inserting a guide wire into a blood vessel in the patient's body. The guide wire is then advanced to the desired location, most commonly in one of the heart vessels or elsewhere in the vascular system. At this point, a catheter is slid over the guide wire into the blood vessel and/or heart. In some procedures, the catheter is a balloon catheter or stent delivery system that when deployed at the site of the lesion allows for increased blood flow through the portion of the coronary artery that is affected by the lesion.

For manual insertion of a guide wire, the physician applies torque and axial push force on the proximal end of a guide wire to effect tip direction and axial advancement at the distal end. Robotic catheter procedure systems have been developed that may be used to aid a physician in performing a catheterization procedure such as a percutaneous coronary intervention (PCI). The physician uses a robotic system to precisely steer a coronary guide wire, balloon catheter or stent delivery system in order to, for example, widen an obstructed artery. In order to perform PCI, the distal tip of a guide wire must be navigated through coronary anatomy past a target lesion. While observing the coronary anatomy using fluoroscopy, the physician manipulates the proximal end of the guide wire in order to direct the distal tip into the appropriate vessels toward the lesion and avoid advancing into side branches.

A robotic catheter procedure system includes various user input device and drive mechanisms to drive various elongated medical devices (e.g., guide wire, guide catheter, working catheter) used in catheterization procedures to provide linear and rotational movement of the elongated medical device. The user input devices may include analog joysticks that are used by an operator of the catheter procedure system to, for example, advance, retract and rotate a percutaneous device, such as a guide wire, a guide catheter or a working catheter. A joystick may experience a fault or failure (e.g., the joystick may be stuck in an "on" state) that may cause a percutaneous device to move in an unexpected manner or may cause the unintended actuation of the percutaneous device when the user is not touching the joystick.

It would be desirable to provide an interlocking system and method for joysticks in a catheter procedure system that provides a single fault safe joystick interface and that provides faster disabling time for halting the motion of the manipulated percutaneous device,

SUMMARY OF THE INVENTION

In accordance with an embodiment, an interlocking system for a joystick in a catheter procedure system, the interlocking system includes a joystick configured to generate a first voltage output signal based on a linear activation of the joystick and a second voltage output signal based on a rotational activation of the joystick, a joystick cover disposed over the joystick and comprising an upper portion having an electrode plating on an inner surface of the upper portion and a lower portion having an inner surface, a capacitive touch detection circuit coupled to the electrode plating of the upper portion of the joystick cover, the capacitive touch detection circuit mounted on the inner surface of the lower portion of the joystick cover and configured to detect a proximal change in capacitance in the electrode plating of the upper portion of the joystick cover and to generate a touch output signal to indicate whether a change in capacitance has been detected, and a signal enable circuit coupled to the joystick and the capacitive touch detection circuit, the signal enable circuit configured to generate a linear enable voltage output signal and a rotational enable voltage output signal based on whether a change in capacitance has been detected.

In accordance with another embodiment, a catheter procedure system includes a bedside system having a percutaneous device and at least one drive mechanism coupled to the percutaneous device and a workstation coupled to the bedside system that includes a joystick configured to generate a first voltage output signal based on a linear activation of the joystick and a second voltage output signal based on a rotational activation of the joystick, a joystick cover disposed over the joystick and comprising an upper portion having an electrode plating on an inner surface of the upper portion and a lower portion having an inner surface, a capacitive touch detection circuit coupled to the electrode plating of the upper portion of the joystick cover, the capacitive touch detection circuit mounted on the inner surface of the lower portion of the joystick cover and configured to detect a proximal change in capacitance in the electrode plating of the upper portion of the joystick cover and to generate a touch output signal to indicate whether a change in capacitance has been detected, and a signal enable circuit coupled to the joystick and the capacitive touch detection circuit, the signal enable circuit configured to generate a linear enable voltage output signal and a rotational enable voltage output signal based on whether a change in capacitance has been detected.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Figure 1:
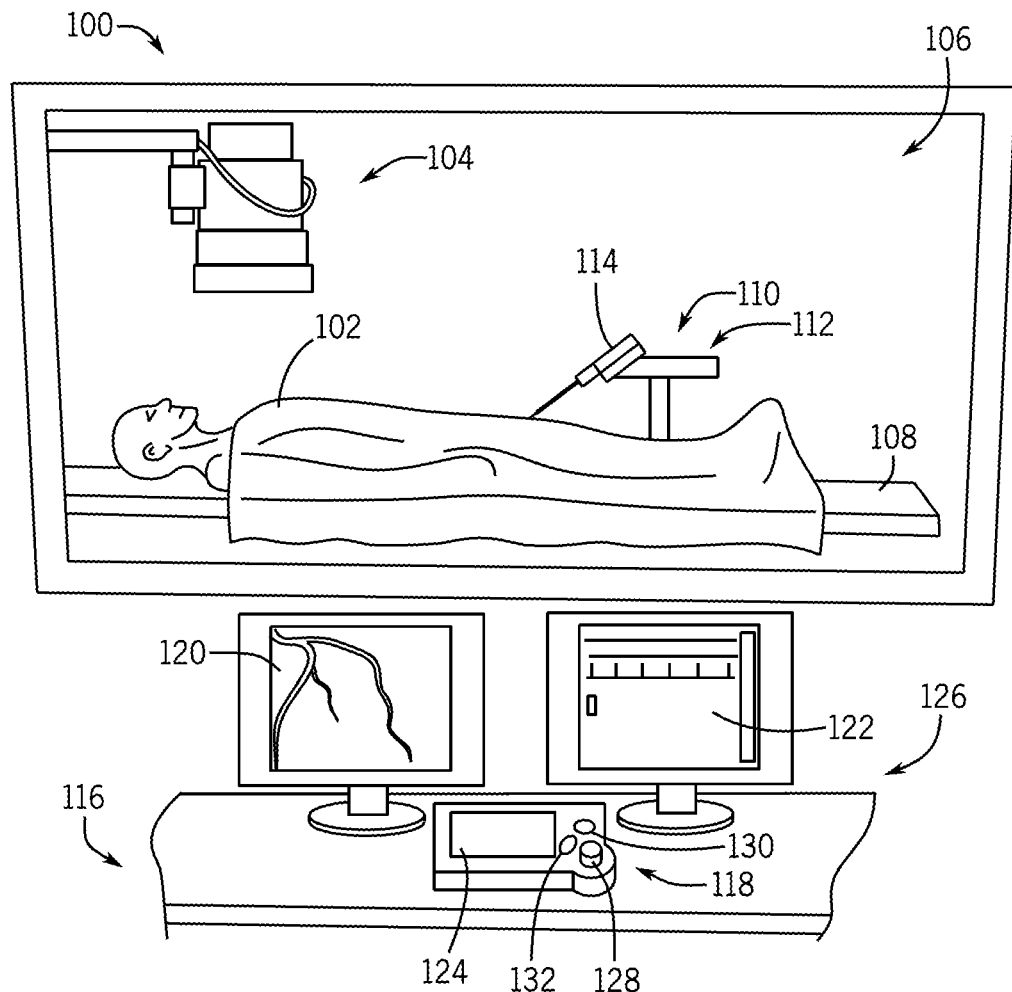
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 describe herein are explained primarily in relation to the treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters such as balloon catheters and stent delivery systems, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a cassette 114 supported by a robotic arm 112 which may be used to automatically advance a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 2) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Cassette 114 includes various drive mechanisms to cause movement (e.g., axial and rotational movement) of the components of the bedside system 110 including the percutaneous devices.

In one embodiment, controls 118 include a touch screen 124, one or more joysticks 128 and buttons 130, 132. The joystick 128 may be configured to advance, retract, or rotate various components and percutaneous devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 2) discussed below. In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

In addition, a user of workstation 116 may be able to control the angular position of imaging system 104 relative to the patient to obtain and display various views of the patient's heart on first monitor 120 and/or second monitor 122. Displaying different views at different portions of the procedure may aid the user of workstation 116 to properly move and position the percutaneous interventional devices within the 3D geometry of the patient's heart. In an embodiment, imaging system 104 may be a 2D imaging system. In another embodiment, imaging system 104 may be any 3D imaging modality such as an x-ray based computed tomography (CT) imaging device, a magnetic resonance imaging device, a 3D ultrasound imaging device, etc. In this embodiment, the image of the patient's heart that is displayed during the procedure may be a 3D image. In addition, controls 118 may also be configured to allow the user positioned at workstation 116 to control various functions of imaging system 104 (e.g., image capture, magnification, collimation, c-arm positioning, etc.).

Figure 2:
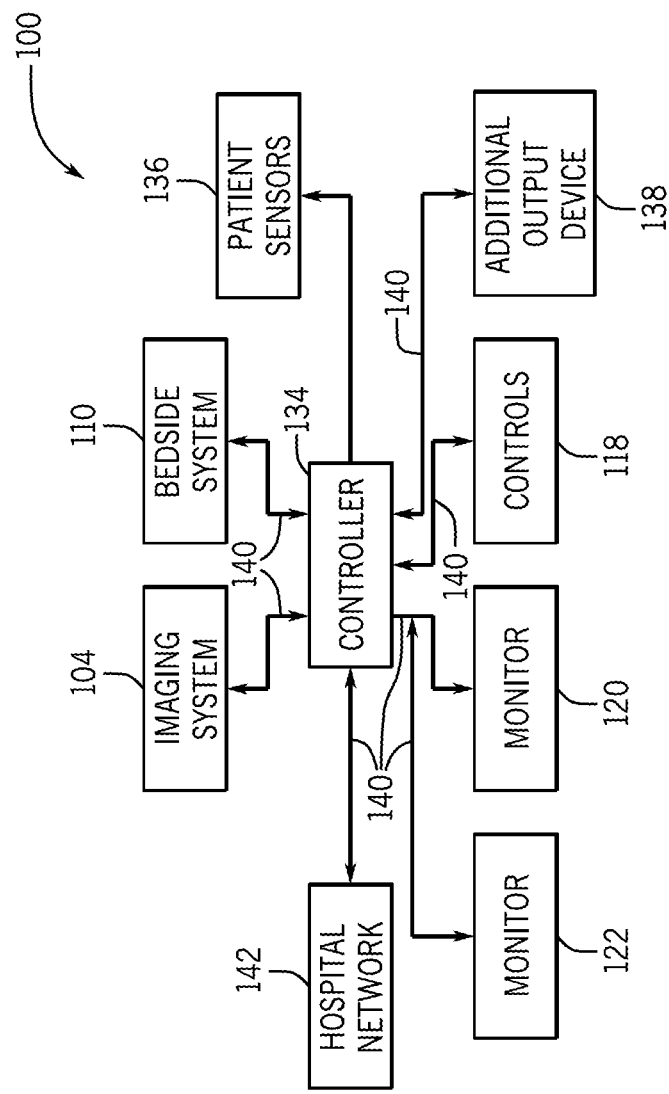
FIG. 2 is a schematic block diagram of a catheter procedure system in accordance with an embodiment.

Referring to FIG. 2, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general purpose system programed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 100, etc.

Figure 3:
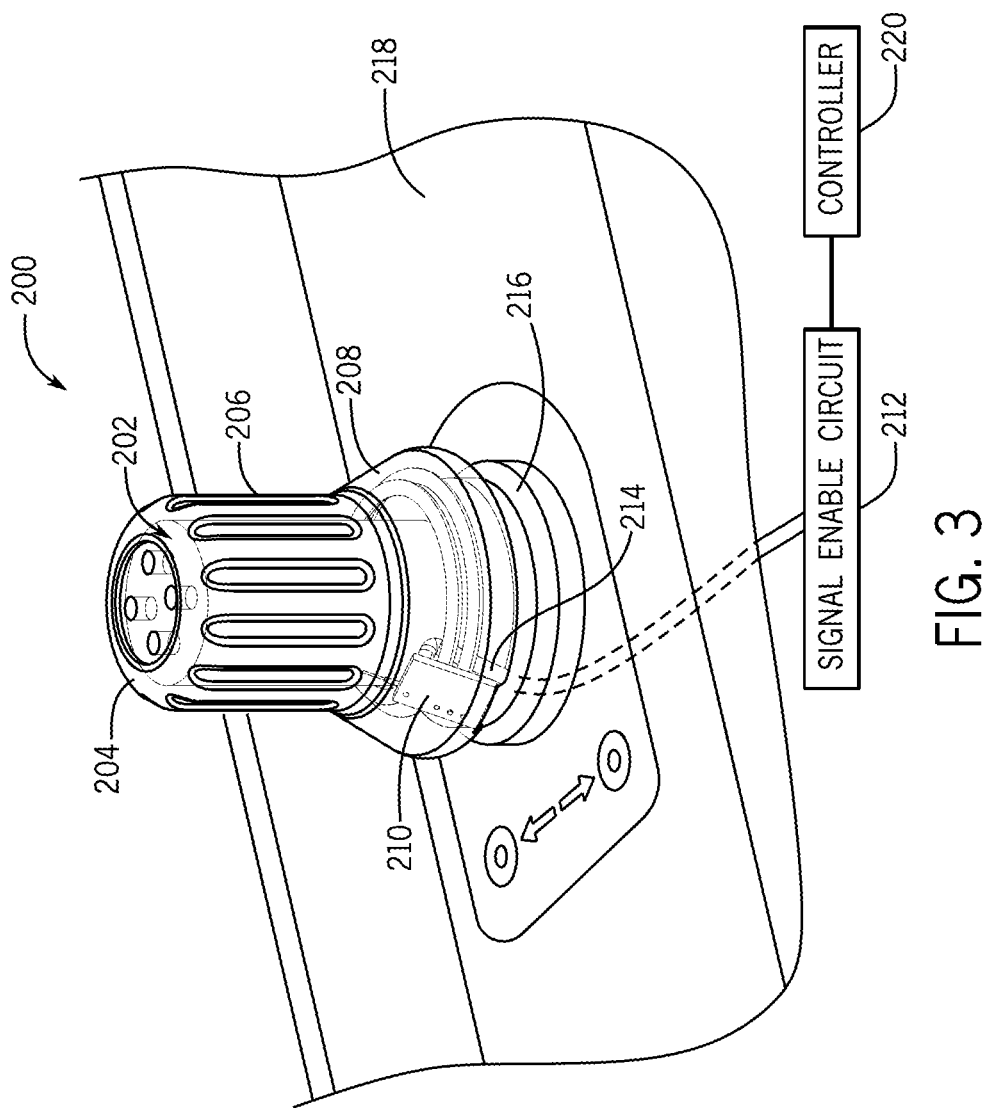
FIG. 3 is a perspective view of an interlocking system in accordance with an embodiment.

As mentioned above, controls 118 of user interface 126 may include one or more joysticks 128 that are used to advance, retract and rotate various components and percutaneous devices such as, for example, a guide wire, a guide catheter or a working catheter. If a joystick 128 experiences a failure while the catheter procedure system is enabled, one of the devices may move in an unintended manner, for example, movement of the device when a user is not touching the joystick. An interlocking system may be provided for joystick 128 to accommodate potential joystick faults and prevent unintended actuation of a device. FIG. 3 is a perspective view of an interlocking system for a joystick in accordance with an embodiment. Interlocking system 200 is a capacitive touch interlocking system and is configured to detect when a user is touching (or making contact with) the joystick and to prevent movement of a percutaneous device if a user is not touching the joystick. Interlocking system 200 is an analog system and does not require software for operation.

In FIG. 3, a joystick 202 is shown as part of a control console 218. The control console 218 may be, for example, a part of the user interface 126 of the workstation 116 shown in FIG. 1. In an embodiment, joystick 202 is an analog joystick configured to generate voltage output signals ($V_{JS-X}$, $V_{JS-Z}$) proportional to the corresponding linear and rotational activation by a user. In one embodiment, the joystick voltage output signals range between a supply voltage ($V_{DD}$) and a ground voltage ($V_{SS}$). A zero position or zero velocity reference voltage ($V_0$) for the joystick 202 may be determined, for example, as half of the sum of the supply voltage and the ground voltage.

$$V_0 = (V_{DD} + V_{SS})/2 \qquad \text{Eqn. 1}$$

The circuitry for joystick 202 may be located inside of the control console 218. Interlocking system 200 includes a joystick cover 204 disposed over the joystick 202. Joystick cover 204 has an upper portion or body 206 and a lower portion or skirt 208. The upper portion 206 of joystick cover 204 is disposed over an upper portion or shaft of joystick 202 and the lower portion 208 of joystick cover 204 is located proximal to a base 216 of joystick 202. In an embodiment, the base 216 of joystick 202 may be surrounded by a carbon boot that is coupled to earth ground. The upper portion 206 of joystick cover 204 is plated with an electrode along an inner surface of the upper portion 206. The lower portion 208 of joystick cover 204 is not plated with an electrode. The electrode plating of the upper portion 206 is coupled to a capacitive touch detection circuit 210 that is positioned on an inner surface of the lower portion 208 of joystick cover 204. Parasitic capacitance may be minimized by positioning the capacitive touch detection circuit on the inner surface of the non-electrode plated lower portion 208 of the joystick cover 204 so that the sense electronics are close to the electrode and at a maximum distance from the ground plane. The electrode plating of upper portion 206 may be coupled to the capacitive touch detection circuit 210 using a conductor that is mounted to the joystick cover 204 using a conductive epoxy. For example a multi-conductor wire may be soldered to the capacitive touch detection circuit 210 and coupled to the electrode plating on the upper portion 206 of the joystick cover 204 using silver conductive epoxy. As discussed further below, capacitive touch detection circuit 210 is configured to detect proximal changes in capacitance from a user touching the joystick 202 and joystick cover 204 with respect to earth ground.

The capacitive touch detection circuit 210 is coupled to a signal enable circuit 212 by a communication link 214, for example, a cable. Communication link 214 is configured to provide power to the capacitive touch sensing circuit 210 such as for example, a supply voltage ($V_{DD}$) and a ground voltage ($V_{SS}$) and to carry voltage signals from the capacitive touch sensing circuit 210 to signal enable circuit 212. Communication link 214 is located proximal to the lower portion 208 of joystick cover 204 and proximal to the base 216 of joystick 202. Signal enable circuit 212 may be located, for example, within the control console 218. Signal enable circuit 212 is also coupled to a controller 220 for the catheter procedure system, for example, controller 134 shown in FIG. 2 and is coupled to joystick 202 to receive the voltage output signals ($V_{JS-X}$, $V_{JS-Z}$) from the joystick 202. Signal enable circuit 212 is configured to route the appropriate joystick voltage signals to the controller 220 based on whether capacitive touch has been detected by the capacitive touch detection circuit 210. Details of the operation of the interlocking system 200 are discussed further below with respect to FIGS. 5-7.

Figure 4:
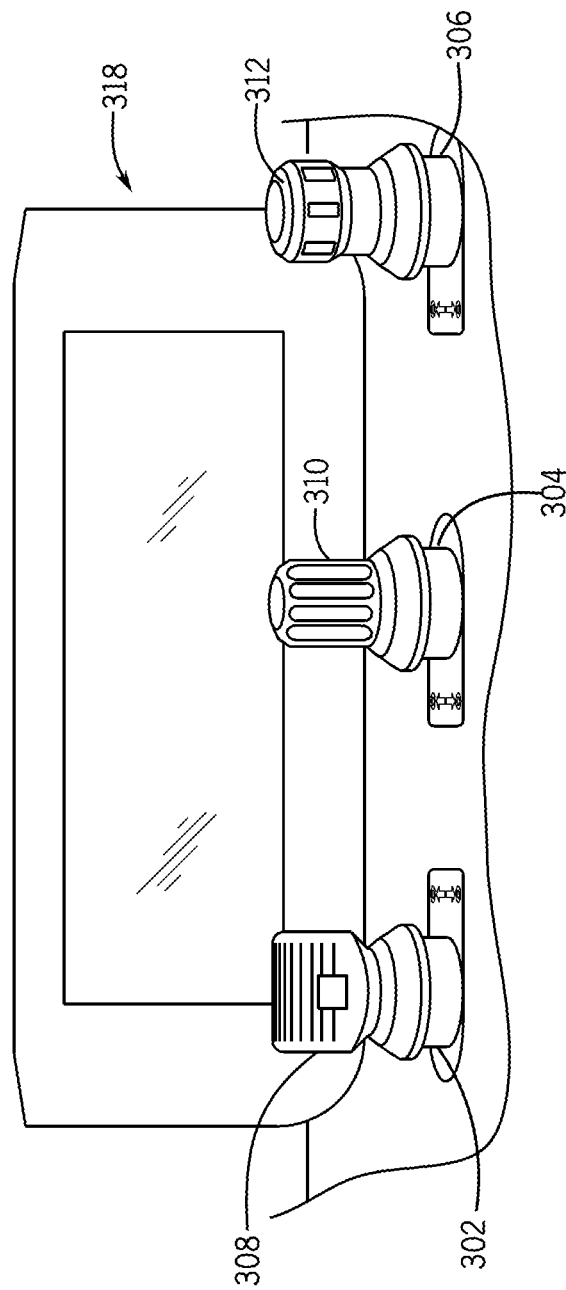
FIG. 4 is a perspective view of multiple joysticks with interlocking systems in accordance with an embodiment.

In an embodiment where more than one joystick is utilized in a catheter procedure system, an interlocking system 200 may be provided for each joystick. FIG. 4 is a perspective view of multiple joysticks with interlocking systems in accordance with an embodiment. In FIG. 4, a control console 318 includes a first joystick 302 with a first interlocking system including an electrode plated joystick cover 308, a second joystick 304 with a second interlocking system including an electrode plated joystick cover 310 and a third joystick 306 with a third interlocking system including an electrode plated joystick cover 312. The first joystick 302 may be used, for example, to control the forward and reverse velocities of a balloon catheter device. The second joystick 304 may be used to, for example, control the forward and reverse velocities and the clockwise and counterclockwise angular velocities of a guide wire. The third joystick 306 may be used to, for example, to control the forward and reverse velocities and the clockwise and counterclockwise velocities of a guide catheter. As mentioned above, the first joystick cover 308, second joystick cover 310 and third joystick cover 312 have an electrode plated upper portion and a lower portion that is not electrode plated.

Figure 5:
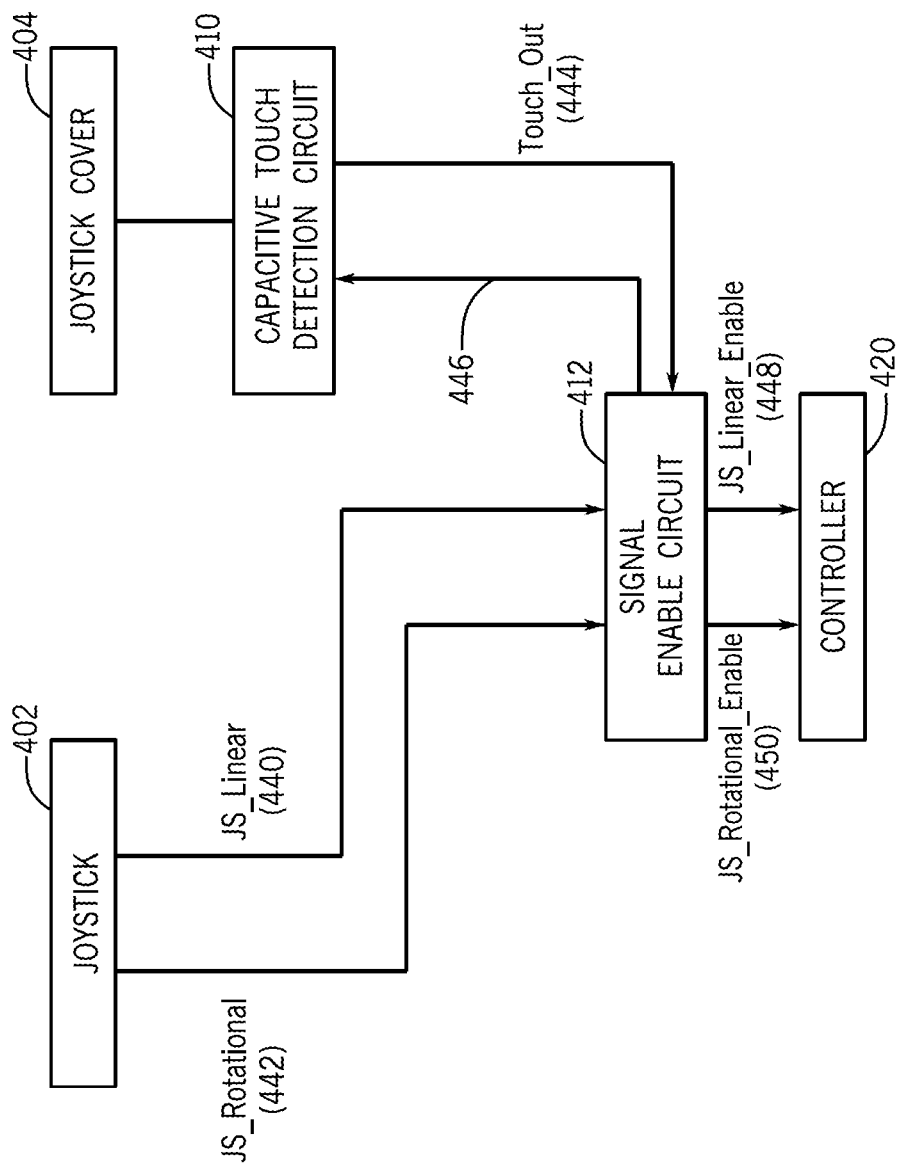
FIG. 5 is a block diagram of an interlocking system in accordance with an embodiment.

FIG. 5 is a block diagram of an interlocking system in accordance with an embodiment. A joystick 402 (e.g., joystick 202 shown in FIG. 3) is used to control the linear velocity (forward and reverse) and the rotational angular velocity (clockwise and counterclockwise) of a device. Joystick 402 is configured to generate voltage output signals proportional to the corresponding activation by a user. In particular, a first joystick voltage output signal 440 (JS_Linear, $V_{JS-X}$) is proportional to the corresponding linear activation by a user. A second joystick voltage output signal 442 (JS_Rotational, $V_{JS-Z}$) is proportional to the corresponding rotational activation by a user. As described above with respect to FIG. 3, a joystick cover 404 is disposed over the joystick 402 and includes an electrode plated upper portion (e.g., upper portion 206 shown in FIG. 3) that is coupled to a capacitive touch detection circuit 410. The electrode plated upper portion of the joystick cover 404 may be coupled to the capacitive touch detection circuit 410 using, for example, a multi-conductor wire that is attached to the joystick cover 404 using, for example, conductive epoxy.

Capacitive touch detection circuit 410 is configured to detect proximal changes in capacitance from a user touching joystick 402 and joystick cover 404 with respect to earth ground. Capacitive touch detection circuit 410 is coupled to a signal enable circuit 412 and receives power signals 446 from the signal enable circuit 412, for example, a supply voltage ($V_{DD}$) and a ground voltage ($V_{SS}$). When touch is detected, the capacitive touch detection circuit 410 generates a touch output signal 444 (Touch_Out) that is, for example, equal to its supply voltage ($V_{DD}$). When touch is not detected, the capacitive touch detection circuit 410 generates a touch output signal 444 (Touch_Out) equal to, for example, the ground voltage ($V_{SS}$). The touch output signal 444 is provided to the signal enable circuit 412. The sensitivity of the capacitive detection circuit 410 may be optimized by selecting a suitable sense capacitor (Cs). Preferably, the layout of the capacitive touch detection circuit 410 is designed to maximize the distance between the touch electrode circuitry from the power and signal planes. This minimizes the parasitic capacitance and results in greater capacitive touch sensitivity.

Both the joystick voltage output voltages (JS_Linear 440 and/or JS_Rotational 442) and the touch output signal 444 (Touch_Out) are provided to the signal enable circuit 412. Signal enable circuit 412 is configured to route the appropriate joystick voltage output signals to the controller 420 based on whether capacitive touch has been detected (i.e., a user is touching the joystick 402 and joystick cover 404) by the capacitive touch detection circuit 410. In an embodiment, if capacitive touch is detected (e.g., Touch_Out=$V_{DD}$), then the signal enable circuit 412 sends enable voltage signals, JS_Linear_Enable 448 and JS_Rotational_Enable 450, equal to the joystick voltage output signals (linear and rotational, respectively) to the controller 420. The enable voltage signals 448 and 450 may be used by controller 420 to control a device based on the user activation of the joystick 402. If capacitive touch is not detected (e.g., Touch_Out=$V_{SS}$), then the signal enable circuit 412 sends enable voltage signals 448 and 450 equal to a predetermined zero velocity reference voltage ($V_0$) so that a device is not actuated.

Figure 6:
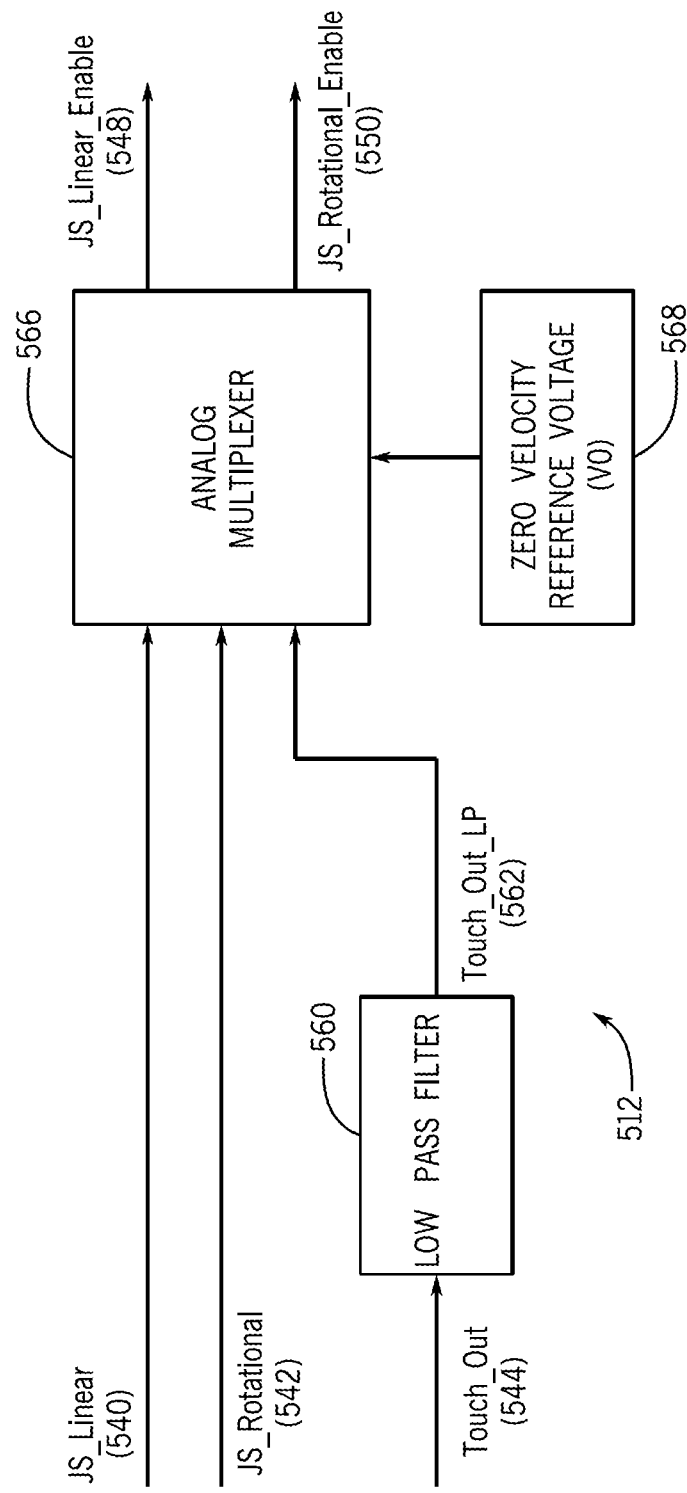
FIG. 6 is a block diagram of a signal enable circuit in accordance with an embodiment.

FIG. 6 is a block diagram of a signal enable circuit 512 in accordance with an embodiment. In FIG. 6, the touch output signal 544 (Touch_Out) is provided to a low pass filter 560.

The low pass filter 560 may be configured to filter out high frequency signals, for example, high frequency heart beat output associated with the capacitive touch output signal 544. The low pass filter 560 generates a filtered touch output signal 562 (Touch_Out_LP). The filtered touch output signal 562 and the joystick voltage output signals 540 and 542 (JS_Linear and JS_Rotational) are provided to an analog multiplexer 566. In addition, the zero velocity reference voltage ($V_O$) 568 is input to the analog multiplexer 566. The analog multiplexer 566 is configured to route the appropriate voltage output signals based on whether capacitive touch has been detected by the capacitive touch detection circuit 410 (shown in FIG. 5). In one embodiment, if capacitive touch has been detected (e.g., Touch_Out_LP=$V_{DD}$), then the analog multiplexer 566 generated enable output signals, JS_Linear_Enable 548 and/or JS_Rotational_Enable 550, equal to the joystick voltage output signals 540 and 542, namely, JS_Linear_Enable=JS_Linear and JS_Rotational_Enable=JS_Rotational. If capacitive touch is not detected e.g., Touch_Out=$V_{SS}$), the analog multiplexer 566 generates enable output signals, JS_Linear_Enable 548 and/or JS_Rotational_Enable 550, equal to the zero velocity reference voltage ($V_O$) 568. The outputs 548 and 550 from the analog multiplexer 566 are provided to the controller 420 (shown in FIG. 5). In an alternative embodiment, if the joystick 402 (shown in FIG. 5) generates a digital output, the multiplexer 566 may be configured to utilize a digital zero velocity reference signal.

Figure 7:
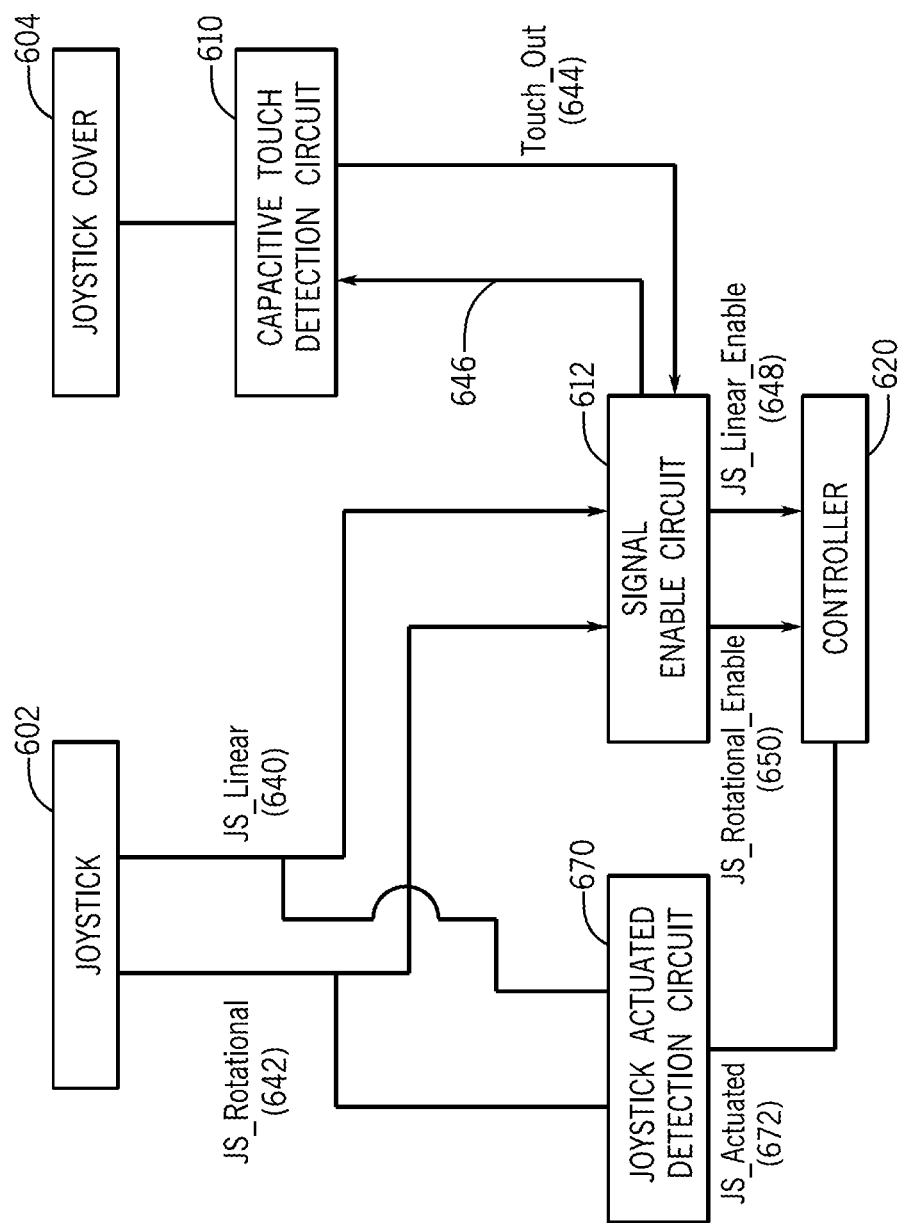
FIG. 7 is a block diagram of an interlocking system and a joystick actuation detection circuit in accordance with an embodiment.

In another embodiment, a joystick actuated detection circuit may also be provided to determine if the joystick 402 (shown in FIG. 5) is in an actuated state. FIG. 7 is a block diagram of an interlocking system and a joystick actuation detection circuit in accordance with an embodiment. As discussed above with respect to FIG. 5, a signal enable circuit 612 routes the appropriate voltage output signals 648, 650 to a controller 620 based on whether capacitive touch has been detected by a capacitive touch detection circuit 610. In the embodiment shown in FIG. 7, the signal enable circuit 612 may also receive an input (JS_Actuated) 672 from a joystick actuated detection circuit 670. The joystick actuated detection circuit 670 is configured to detect whether the linear axis of the joystick 602 (e.g., joystick 202 shown in FIG. 3) or the rotational axis of the joystick 602 is outside of a predetermined dead band of the joystick 602. Accordingly, the joystick actuated detection circuit 670 receives as inputs the voltage output signals, JS_Linear 640 and JS_Rotational 642, and monitors the voltage output signals 640 and 642. In one embodiment, if either the linear voltage output signal 640 or the rotational voltage output signal 642 deviates more than a dead band voltage ($V_{dead-band}$) from the zero velocity reference voltage ($V_O$) then the joystick actuated detection circuit 670 generates a joystick actuated output signal 672 (JS_Actuated) that is set to a value of true (e.g., JS_Actuated=1). If the voltages output signals 640 and 642 do not deviate from the zero velocity reference voltage ($V_O$) by more than the dead band voltage, then the joystick actuated detection circuit 670 generates a joystick actuated output signal 672 (JS_Actuated) that is set to a value of false (e.g., JS_Actuated=0). The joystick actuated output signal 672 may be used by signal enable circuit 612 to identify if joystick 602 is in a faulty state before actuation. Signal enable circuit 612 may use the joystick actuated output signal 672 along with the touch output signal 644 to generate a signal that may be used to activate an imaging system (e.g., imaging system 104 shown in FIG. 1). For example, a signal may be generated based on the touch output signal 644 and the joystick actuated output signal 672 to activate the imaging system to begin taking images before a device (e.g., a guide wire, a guide catheter, a working catheter) is actuated.

In one embodiment, the joystick actuated detection circuit 670 may include three subsystems to monitor the joystick voltage output signals 640 and 642 and generate the joystick actuated output signal 672. For each subsystem, a lower reference voltage ($V_{LR}$) is set as:

$$V_{LR} = V_0 - V_{dead-band} \quad \text{Eqn. 2}$$

and an upper reference voltage ($V_{UR}$) is set as:

$$V_{UR} = V_0 + V_{dead-band} \quad \text{Eqn. 3}$$

A first subsystem monitors the linear joystick voltage output signal 640 to determine if the linear joystick output voltage 640 deviates from the zero velocity reference voltage ($V_O$) by more than the dead band voltage. If the linear voltage output signal 640 (JS_Linear) is less than the upper reference voltage ($V_{UR}$), then the (L)ess (Than) (U)pper (R)eference signal (Linear_LT-UR) is set to a value of true (e.g., Linear_LT-UR=1), otherwise the less than upper reference signal is set to a value of false (e.g., Linear_LT-UR=0). If the linear voltage output signal 640 (JS_Linear) is greater than the lower reference voltage ($V_{LR}$), then a (Greater) (T)han (L)ower (R)eference signal (Linear_GT-LR) is set to a value of true (e.g., Linear_GT-LR=1), otherwise the greater than lower reference signal is set to a value of false (e.g., Linear_GT-LR=0). A resulting output signal of this linear subsystem (Linear_Y) is set to a value of true (e.g., Linear_Y=1) if either the less than upper reference signal (Linear_LT-UR) or the greater than lower reference signal (Linear_GT-LR) is false, otherwise the resulting output signal is set to a value of false (e.g., Linear_Y=0). These relationships are summarized in Table 1.

TABLE 1

| JS_Linear to Linear_Y Logic Table. | | | |
|---|---|---|---|
| Condition | Linear LT-UR | Linear GT-LR | Linear_Y |
| JS_Linear ≤ $V_{LR}$ (outside deadband) | 1 | 0 | 1 |
| $V_{LR}$ < JS_Linear < $V_{UR}$ (within deadband) | 1 | 1 | 0 |
| $V_{UR}$ ≤ JS_Linear (outside deadband) | 0 | 1 | 1 |

A second subsystem monitors the rotational joystick voltage output signal 642 to determine if the rotational joystick output voltage 642 deviates from the zero velocity reference voltage ($V_O$) by more than the dead band voltage. If the rotational voltage output signal 642 (JS_Rotational) is less than the upper reference voltage ($V_{UR}$), then the (L)ess (T)han (U)pper (R)eference signal (Rotational_LT-UR) is set to a value of true (e.g., Rotational_LT-UR=1), otherwise the less than upper reference signal is set to a value of false (e.g., Rotational_LT-UR=0). If the rotational voltage output signal 642 (JS_Rotational) is greater than the lower reference voltage ($V_{LR}$), then a (G)reater (T)han (L)ower (R)eference signal (Rotational_GT-LR) is set to a value of true (e.g., Rotational_GT-LR=1), otherwise the greater than lower reference signal signal is set to a value of false (e.g., Rotational_GT-LR=0). A resulting output signal of this rotational subsystem (Rotational_Y) is set to a value of true (e.g., Rotational_Y=1) if either the less than upper reference signal (Rotational_LT-UR) or the greater than lower reference signal (Rotational_GT-LR) is false, otherwise the resulting output signal is set to a value of false (e.g., Rotational_Y=0). These relationships are summarized in Table 2.

TABLE 2

JS_Rotational to Rotational_Y Logic Table

| Condition | Rotational LT-UR | Rotational GT-LR | Rotational_Y |
|---|---|---|---|
| JS_Rotational ≤ $V_{LR}$ | 1 | 0 | 1 |
| $V_{LR}$ < JS_Rotational < $V_{UR}$ | 1 | 1 | 0 |
| $V_{UR}$ ≤ JS_Rotational | 0 | 1 | 1 |

In one embodiment, the logic presented in Table 1 and Table 2 may be implemented using either analog comparators and corresponding digital logic elements or a mixed signal digital signal processor (DSP) with either four comparator or analog inputs and two corresponding digital outputs for the Linear_Y and Rotational_Y outputs.

A third subsystem generates the joystick actuated output signal 672 based on the values of the linear subsystem output signal (Linear_Y) and the rotational subsystem output signal (Rotational_Y). If either the linear subsystem output signal (Linear_Y) or the rotational subsystem output signal (Rotational_Y) is true, then the joystick actuated output signal 672 is set to a value of true (e.g., JS_Actuated=1), otherwise the joystick actuated output signal 672 is set to a value of false (e.g., JS_Actuated=0). The joystick actuated output signal 672 is provide to the signal enable circuit 612.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

What is claimed is:

1. A user interface for a robotic medical system, the user interface comprising:
    an interlocking system including an input device configured to control a percutaneous device based on a physical activation of the input device;
    the interlocking system including a capacitive touch detection circuit operatively coupled to a cover of the input device detecting when a user is touching the cover, the interlocking system being configured to detect operation of the input device by the user, wherein the interlocking system is configured to prevent movement of the percutaneous device when the user is not touching the cover of the input device.

2. The user interface according to claim 1, wherein the interlocking system is configured to allow movement of the percutaneous device based on activation of the input device when the operation of the input device by the user is detected.

3. The user interface according to claim 1, wherein the input device is an analog joystick.

4. The user interface according to claim 1, wherein:
    the input device cover being disposed over the input device and comprising a first portion having an electrode plating on the first portion;
    the capacitive touch detection circuit operatively coupled to the input device cover, and configured to detect a proximal change in capacitance in the electrode plating of the first portion of the input device cover and to generate a touch output signal to indicate whether the change in capacitance has been detected; and
    a signal enable circuit coupled to the input device and the capacitive touch detection circuit, the signal enable circuit configured to generate an enable voltage output based on whether a change in capacitance has been detected.

5. The user interface according to claim 4, wherein the capacitive touch detection circuit is positioned intermediate the first portion of the cover and the input device.

6. The user interface according to claim 5, wherein the capacitive touch detection circuit is coupled to the electrode plating of the first portion of the input device cover using a conductor mounted to the input device cover using a conductive adhesive.

7. A catheter procedure system comprising:
    a bedside system comprising at least one drive mechanism configured to control a percutaneous device; and
    an interlocking system coupled to the bedside system, the interlocking system including an input device configured to control the percutaneous device, via the bedside system, based on a physical activation of the input device;
    the interlocking system including a capacitive touch detection circuit operatively coupled to a cover of the input device detecting when a user is touching the cover, the interlocking system being configured to detect operation of the input device by a user, wherein the interlocking system is configured to prevent movement of the percutaneous device when the user is not touching the cover of the input device.

8. The catheter procedure system according to claim 7, wherein the interlocking system is configured to allow movement of the percutaneous device based on activation of the input device when the operation of the input device by the user is detected.

9. The catheter procedure system according to claim 7, wherein the input device is an analog joystick.

10. The catheter procedure system according to claim 7, wherein
    the cover of the input device being disposed over the input device and comprising a first portion having an electrode plating on the first portion;
    the capacitive touch detection circuit operatively coupled to the input device cover, and configured to detect a proximal change in capacitance in the electrode plating of the first portion of the input device cover and to generate a touch output signal to indicate whether the change in capacitance has been detected; and
    a signal enable circuit coupled to the input device and the capacitive touch detection circuit, the signal enable circuit configured to generate an enable voltage output based on whether the change in capacitance has been detected.

11. The catheter procedure system according to claim 10, wherein the capacitive touch detection circuit is positioned intermediate the first portion of the cover and the input device.

12. The catheter procedure system according to claim 11, wherein the capacitive touch detection circuit is coupled to the electrode plating of the first portion of the input device cover using a conductor mounted to the input device cover using a conductive adhesive.

13. A method of controlling a robotic medical system comprising an interlocking system having a capacitive detection circuit and an input device, the interlocking system configured to control a percutaneous device based on a physical activation of the input device, the method comprising:
  receiving a command for an actuating movement of the percutaneous device based on the physical activation of the input device by a user;
  determining whether the physical activation of the input device is detected by the interlocking system; and
  preventing movement of the percutaneous device by the interlocking system when the interlocking system determines that the user is not touching a cover of the input device.

14. The method according to claim 13, further comprising:
  allowing movement of the percutaneous device by the interlocking system when the interlocking system determines operation of the input device by the user is detected.

15. The method according to claim 13, wherein the input device is an analog joystick.

16. The method according to claim 13, wherein
  the cover of the input device being disposed over the input device and comprising a first portion having an electrode plating on the first portion;
  the capacitive touch detection circuit operatively coupled to the cover of the input device, and configured to detect a proximal change in capacitance in the electrode plating of the first portion of the input device cover and to generate a touch output signal to indicate whether the change in capacitance has been detected; and
  a signal enable circuit coupled to the input device and the capacitive touch detection circuit, the signal enable circuit configured to generate an enable voltage output based on whether the change in capacitance has been detected.

17. The method according to claim 16, wherein the capacitive touch detection circuit is positioned intermediate the first portion of the cover and the input device.

18. The method according to claim 17, wherein the capacitive touch detection circuit is coupled to the electrode plating of the first portion of the input device cover using a conductor mounted to the input device cover using a conductive adhesive.

* * * * *